United States Patent [19]

Chiang

[11] Patent Number: 5,894,606
[45] Date of Patent: Apr. 20, 1999

US005894606A

[54] SWIMMING GOGGLE

[76] Inventor: Herman Chiang, 11F-2, No. 634-9, Ching-Ping Road, Chung-Ho City, Taiwan

[21] Appl. No.: 08/959,780

[22] Filed: Oct. 29, 1997

[51] Int. Cl.⁶ .................................................. A61F 9/02
[52] U.S. Cl. ...................................... 2/440; 2/426
[58] Field of Search ............................. 2/428, 440, 441, 2/426, 427, 429, 430, 447, 443, 444, 454

[56] References Cited

U.S. PATENT DOCUMENTS

| | | | |
|---|---|---|---|
| 295,242 | 3/1884 | Genese | 2/440 |
| 1,146,549 | 7/1915 | Brayton | 2/440 |
| 2,393,533 | 1/1946 | Heinz | 2/440 |
| 2,593,892 | 4/1952 | Kindel | 2/428 |
| 3,725,953 | 4/1973 | Johnson et al. | 2/428 |

*Primary Examiner*—Michael A. Neas
*Assistant Examiner*—Larry D. Worrell, Jr.
*Attorney, Agent, or Firm*—Pro-Techtor Inter-National Services

[57] ABSTRACT

A swimming goggle structure includes two lens frames each having a lens fixed thereon, a nose bridge connecting between inner sides of the lens frames and a head strap connecting between outer sides of the lens frames. Each of the lens frames has a cushion pad provided on a wearer facing side thereof and the cushion pad includes a connection portion at is attached to the respective lens frames of the swimming goggle structure and a cushion body which is a hollow sealed member with air filled therein to provide compressibility and collapsibility. The cushion body has a face engaging surface which is capable to very comfortably engage with the wearer's face due to the collapsibility thereof and to very compliantly follow the wearer's face contour for an excellent water leakage proofness due to the compressibility thereof.

16 Claims, 6 Drawing Sheets

(II-II)

SWIMMING GOGGLE

FIELD OF THE INVENTION

The present invention relates generally to swimming goggles and in particular to a swimming goggle structure that incorporates an air cushion pad for a more comfortable and compliant engagement with the wearer's face.

BACKGROUND OF THE INVENTION

To provide a comfortable engagement with the wearer's face, swimming goggles are usually provided with a cushion pad of resilient material mounted to each of the lens frames of the goggles to be in resilient contact with the wearer's face around the eye sockets. Conventionally, the swimming goggle cushion pads have two types. The first one is made of a foamed material and the second one comprises a collapsible suction cup like confirmation made of a resilient material. These two different types of cushion pad provide different capabilities in comfort of face engagement and leakage proofness. The foamed material type cushion pad, although being made as a block, offers a very comfortable engagement with the wearer's face due to the soft nature of the foam material used to make the cushion pad. In addition, the foamed material that is used to make the cushion pad also allows heat generated by the wearer's face skin to be dissipated so that an even greater comfort may be provided to the wearer's face skin. However, due to the fact that the foamed material that is used to make the cushion pad is generally in the form of a block which does not allow an excellent compliance with the face contour of the wearer so as not to provide a good leakage proof engagement with the wearer's face. Thus leakage may occur and water may gradually get into the swimming goggles.

The suction cup type cushion pad is usually made of rubber or non-foamed thermoplastic plastics which provides an excellent water leakage proof property. The suction cup type cushion pad usually has a J-shaped cross section hang a very thin flange for face contact engagement which allows an instant collapse upon contact with the wearer's face so as to be very compliant to the wearer's face contour for an excellent water leakage proofness. The suction cup type cushion pad, although possessing a good water leakage proof property, yet may not be suitable for everybody's face contour for the face contour is different from person to person. Water leakage problem is thus not completely overcome by the collapsible suction cup type cushion pad.

Thus, it is desired to provide an air cushion pad for swimming goggles which has the advantages of both the foamed material type cushion pad and the collapsible suction cup type cushion pad so as to overcome the problems encountered in the prior art.

SUMMARY OF THE INVENTION

An object of the present invention is to provide an air cushion type swimming goggle cushion pad, which by means of the compressibility and fluid flow characteristics of the air filled in the cushion pad, provides an excellent compliant engagement with the wearer's face contour that is not only capable to accommodate different face contours, but may also very comfortably engages the wearer's face to provide a very comfortable and very water leakage proof swimming goggle cushion pad structure.

Thus, to achieve the above objects, in accordance with the present invention, an air cushion pad structure of swimming goggles is provided, comprising a connection portion that is attached to each of the lens frames of the swimming goggles and a cushion body which is a hollow sealed member with air filled therein to provide compressibility and collapsibility. The cushion body has a face engaging surface which is capable to very comfortably engage with the wearer's face due to the collapsibility thereof and to very compliantly follow the wearer's face contour for an excellent water leakage proofness due to the compressibility thereof.

In accordance with the present invention, the face engaging surface of the cushion body has an arc configuration to provide an even better compliance with the wearer's face contour.

The objects, advantages and features of the present invention will be apparent from the following description of preferred embodiments thereof, with reference to the attached drawings, wherein:

DETAILED DESCRIPTION OF THE PREFERRED EMBODIMENTS

Figure 1:
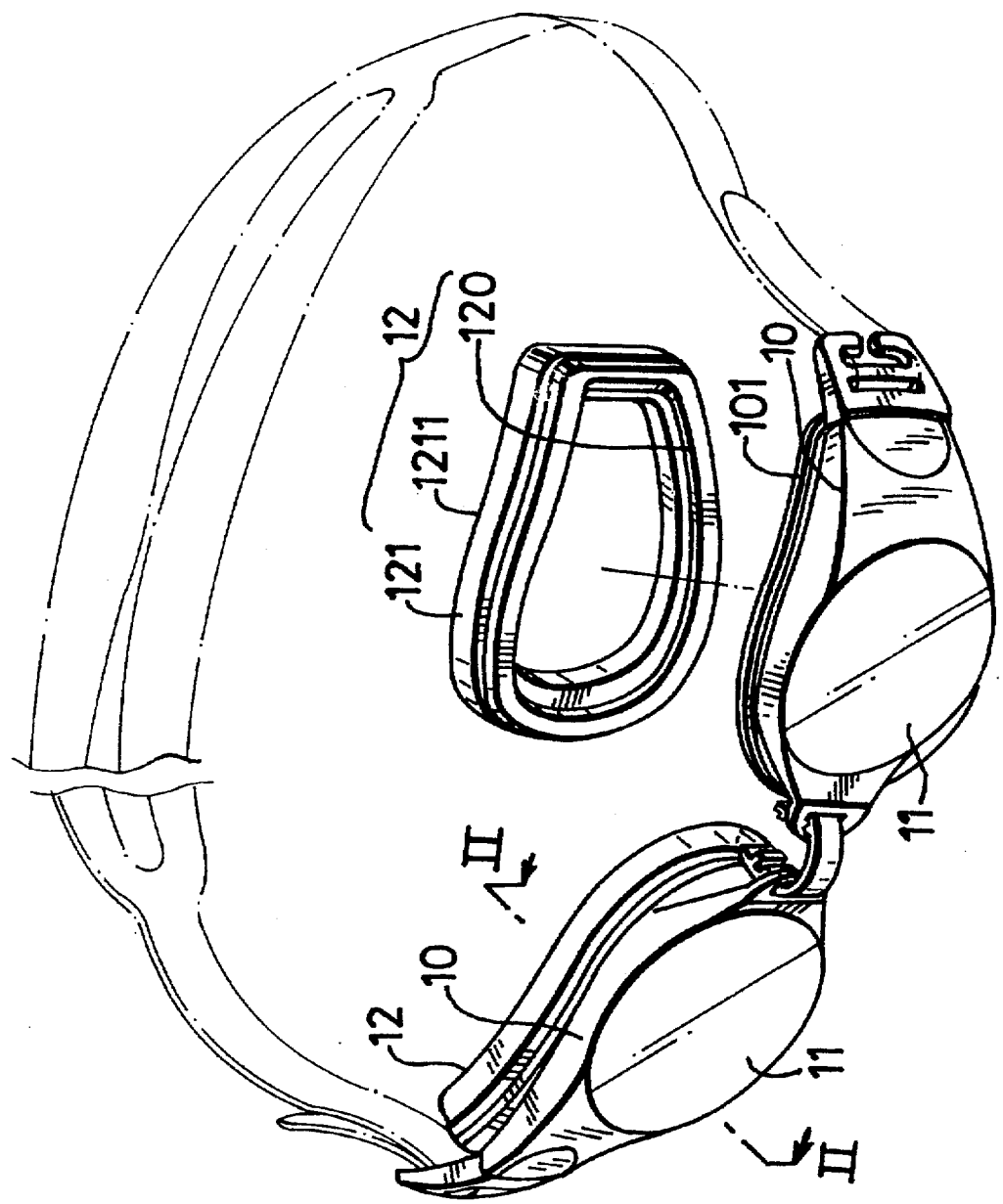
FIG. 1 is a perspective view, partially exploded, showing a pair of swimming goggles on which an air cushion pad structure in accordance with the present invention is mounted.
Figure 2:
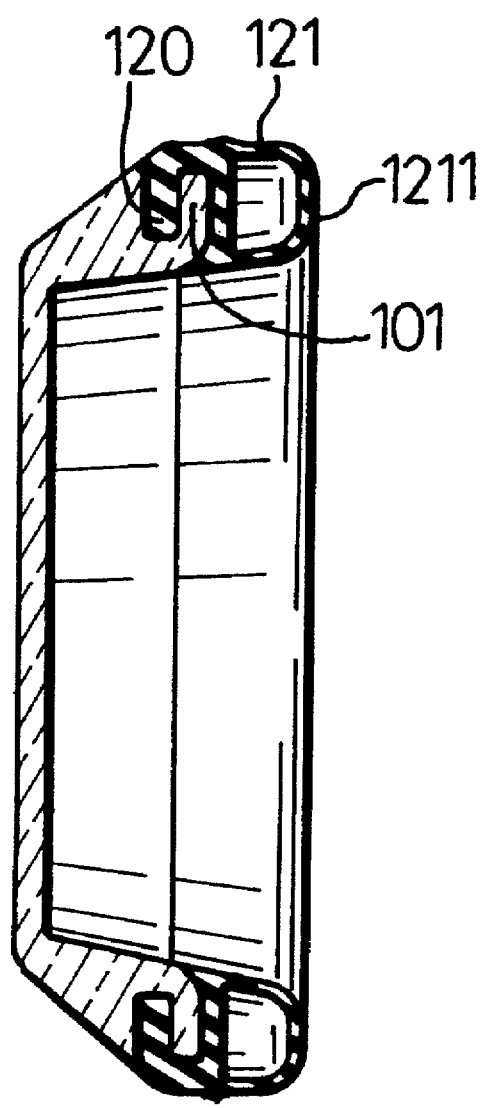
FIG. 2 is a cross-sectional view taken along line II—II in FIG. 1.

Referring to the drawings and in particular to FIG. 1, wherein a pair of swimming goggles incorporating an air cushion pad constructed in accordance with a first embodiment of the present invention is shown, the swimming goggles, which are designated with reference numeral 1, comprises two lens frames 10, each comprising a lens 11 integrally formed therewith or separately formed and mounted thereto. The lens frames 10 has an inner side connected to each other by means of a nose bridge and an outer side connected to each other by means of a head strap. Each of the lens frames 10 has a cushion pad 12 mounted thereto. In accordance with the present invention, the cushion pad 12 comprises an air cushion like configuration, comprising a connection portion 120 and a cushion body 121. Also referring to FIG. 2, the cushion body 121 has a thickness ranging between 0.5–2 mm and a preferred thickness is 0.6 mm, comprising a hollow enclosure structure having a sealed space therein into which air or other gas is filled. The hollow structure of the cushion body 121 is made flexible and resilient and is connected to or integrally formed with the connection portion 120. The cushion body 121 comprises an arc contact surface or face engaging surface 1211 to be in contact engagement with a wearer's face. The connection portion 120 comprises a circumferential slot sized and positioned to be fit onto a raised circumferential rib 101 around the lens frame 10, see FIG. 2. The flexible hollow structure of the cushion body 121 having air filled therein allows the cushion body 121 to be collapsible and compressible so as to provide both a more tight and a more compliant contact engagement with the wearer's fake and a leakage proof and comfortable engagement is provided between the wearer's face and the contact surface 1211. In other words, the collapse of the cushion body 121 makes the face engaging surface 1211 to be very compliant to the wearer's face contour when the contact surface 1211 is brought into contact with the wearer's face. Further, the flexible hollow structure of the cushion body 121 allows the face engaging surface 1211 to accommodate different face contours to provide a comfortable and leakage proof engagement with the wearer's face.

Figure 3:
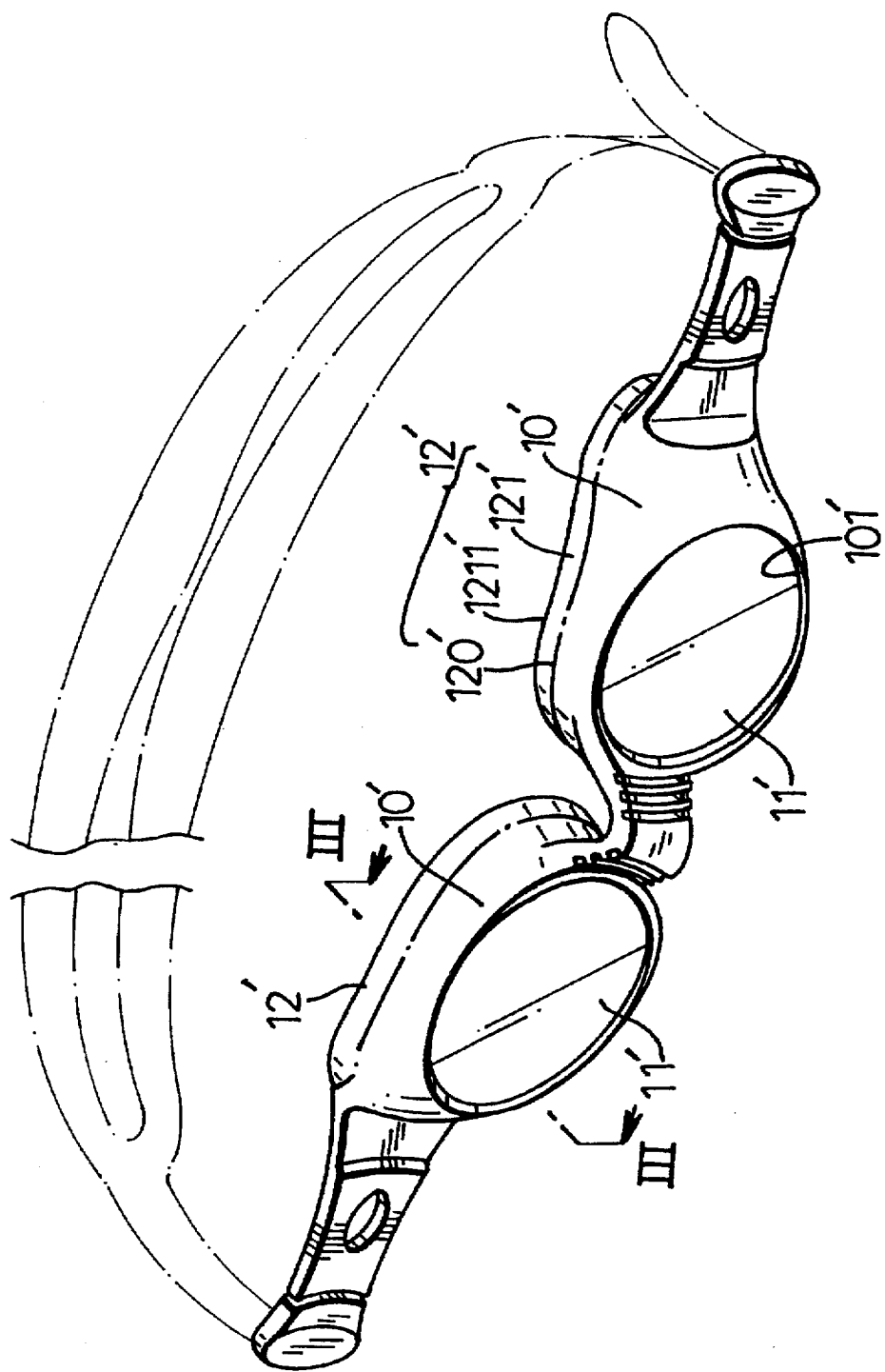
FIG. 3 is a perspective view showing a pair of swimming goggles in which an air cushion pad in accordance with a second embodiment of the present invention is incorporated.
Figure 4:
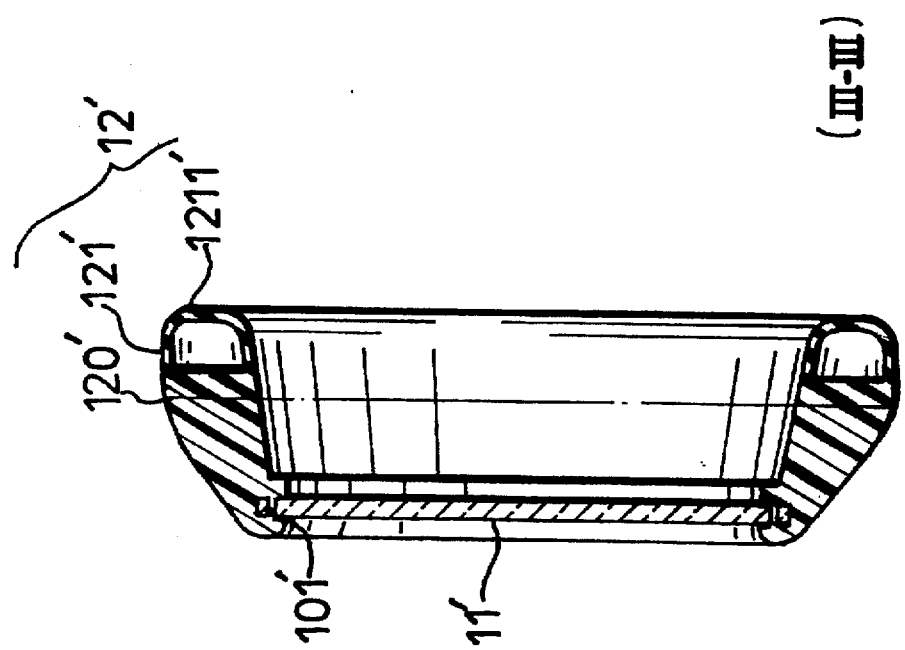
FIG. 4 is a cross-sectional view taken along line III—III of FIG. 3.

With reference to FIG. 3, which shows a second embodiment in accordance with the present invention, in the swimming goggles of the present invention, an air cushion pad 12' is integrally formed with each of the lens frames 10' and each of the lens frames 10' comprises an inner circumferential groove 101' within which a lens 11' is received and fixed. Further referring to FIG. 4, the air cushion pad 12' of the second embodiment is similar to that of the first embodiment illustrated above and comprises a connection portion 120' and a cushion body 121'. Also see FIG. 2, the cushion body 121' has a thickness ranging between 0.5–2 mm and preferably 0.6 mm, comprising a hollow enclosure structure having a sealed space therein filled with a gas, such as air. The hollow enclosure structure is made flexible and resilient and is connected to or integrally formed with the connection portion 120'. The cushion body 120' comprises an arc face engaging surface 1211' to be in contact engagement with the wearer's face. The connection portion 120' is integrally formed with the lens frame 10' which is formed by using a mold to form the cushion pad 12' as a hollow configuration and connecting to the lens frame 10' during the curing process of the material (such as rubber) that makes the lens frame 10'. Similar to the first embodiment, the flexible hollow structure of the cushion body 1211 allows the cushion body 121 to be compliant with the wearer's face contour and providing a good leakage proof property.

Figure 5:
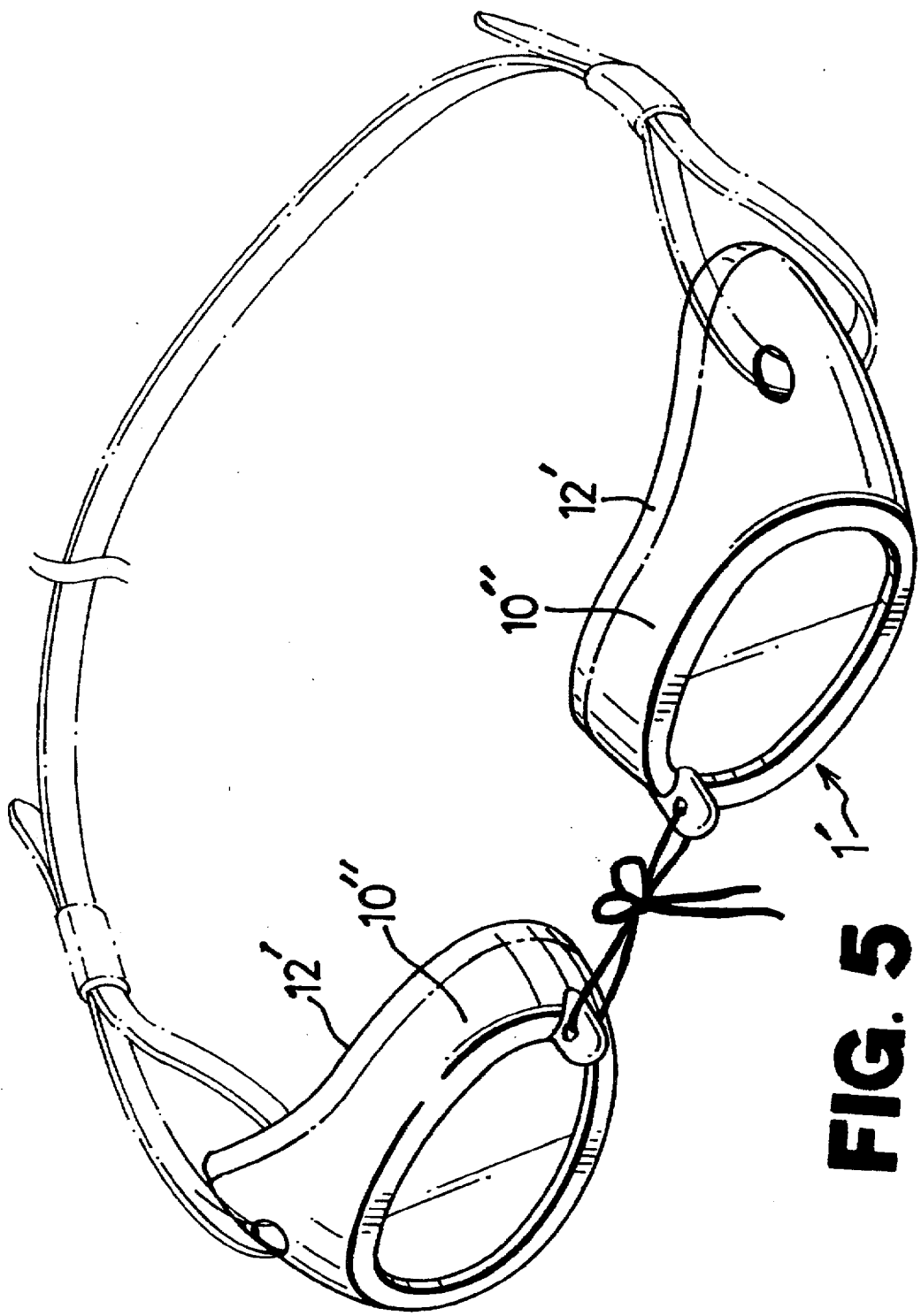
FIG. 5 is a perspective view showing a pair of swimming goggles incorporating the air cushion pad of the present invention.

With reference to FIG. 5 which shown a different embodiment of the present invention, a pair of swimming goggles 1' that have a slightly different structure from those shown in FIGS. 1–4 in an overall configuration, comprise two lens frames 10" with which an air cushion pad 12' in accordance with the present invention is integrally formed so as to provide a comfortable and water leakage proof contact engagement with the wearer's face. The compressibility and collapsibility of the air cushion pad 12' allows the cushion pad to be capable to accommodate different face contours and to provide an excellent water leakage proofness.

Figure 6:
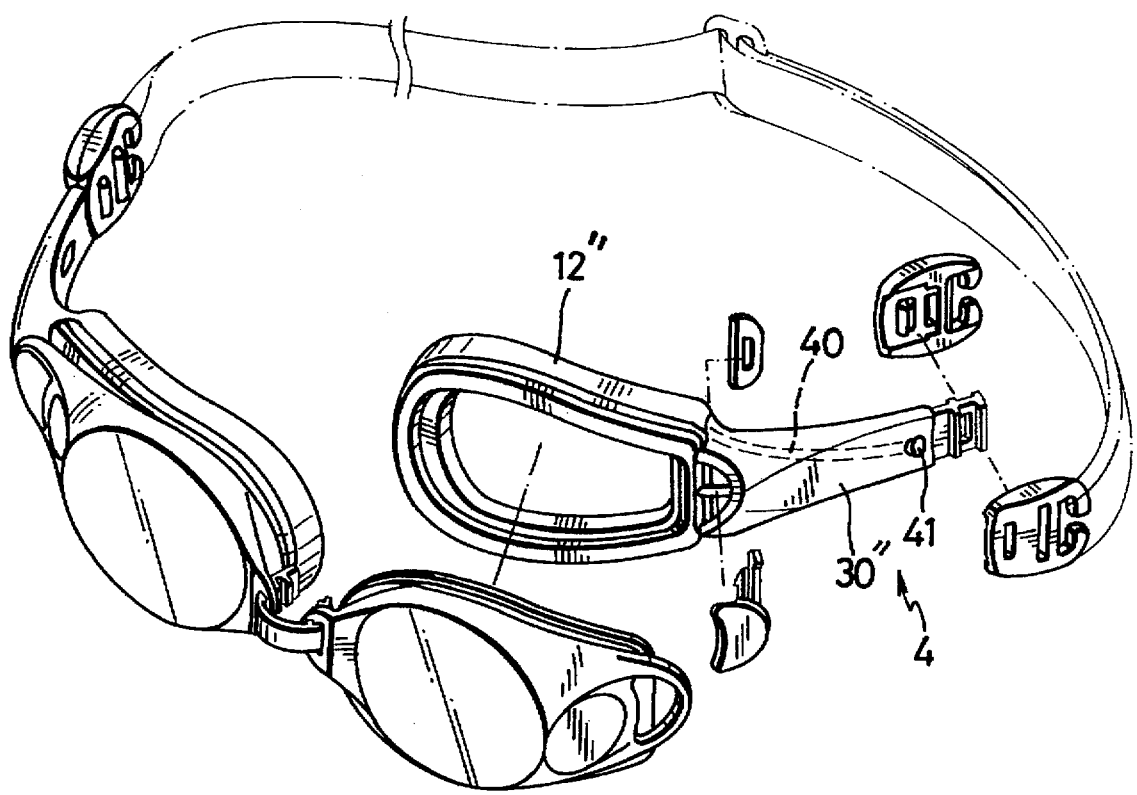
FIG. 6 is a perspective view, partially exploded, showing a pair of swimming goggles on which an air cushion pad for swimming goggles in accordance with a further embodiment of the present invention is mounted.

With reference to FIG. 6 which shows an air cushion pad 12" made in accordance with a further embodiment of the present invention, the air cushion pad 12" of the further embodiment is similar to that of the first embodiment with a circumferential slot formed around the cushion pad to be fit onto a rib formed on the respective lens frame. In the embodiment of FIG. 6, the air cushion 12" further comprises an extension 30" having a remote end to which the head strap may be coupled. An inflating device 4 is mounted on the extension 30" and comprises an inlet 41 formed on the extension 30", preferably at the remote end of the extension 30" and a gas passage 40 extending from the inlet 41 and communicating with the sealed enclosure of the air cushion 12" to allow the gas or air to be filled into the air cushion 12" via the inlet 41 and the passage 40. The extension 30" may comprise an anti-stretching device provided thereon with the inlet 41 formed on the anti-stretching device.

Alternatively, each of the lens frames may comprise an anti-stretching extension at the outer end of the lens frame which protects the lens frames from being stretched when the swimming goggles are worn. The anti-stretching extension has a remote end to be coupled by the head strap.

The cushion body and the connection portion may be made of a same material, but are preferably made of materials of different rigidities. Namely, the cushion body may be made of a softer rubber material and the connection portion made of a more rigid material. Both materials may be rubber materials.

Further, if desired, the connection portion and the cushion body may be differently colored so as to provide a visual indication and attraction.

The above description is made with respect to the preferred embodiments of the present invention and for those skilled in the art, it is possible to make a variety of modifications and changes to the above-described specific embodiments without departing from the scope and spirit of the present invention. All these modifications and changes should be considered within the scope of the present invention as defined in the appended claims.

What is claimed is:

1. A swimming goggle structure comprising:

two lens frames each holding therein a lens, a nose bridge connecting inner sides of the lens frames, and a head strap connecting outer sides of the lens frames, each of the lens frames having a side adapted to face a wearer's face and comprising an air cushion pad mounted thereto, said air cushion pad comprising a connection portion which is connected to the lens frame and a cushion body attached to the connection portion, the cushion body comprising a hollow sealed configuration that is collapsible with a gaseous material filled therein, the cushion body having a face engaging surface adapted to be in contact with the wearer's face, and wherein the connection portion is made of a first rubber material and the cushion body is made of a second rubber material, the first rubber material being comprised entirely of a material that is uniformly thicker and more rigid than the second rubber material.

2. The swimming goggle structure as claimed in claim 1, wherein the face engaging surface of the cushion body has an arc shape to comply with contour of the wearer's face.

3. The swimming goggle structure as claimed in claim 2, wherein the cushion body has a thickness between 0.5–2 mm.

4. The swimming goggle structure as claimed in claim 3, wherein the connection portion is made of a first rubber material having a first color and the cushion body is made of a second rubber material having a second color which is different from the first color.

5. The swimming goggle structure as claimed in claim 4, wherein the cushion body further comprises inflating means for filling the gaseous material into the cushion body.

6. The swimming goggle structure as claimed in claim 5, wherein the connection portion is integrally formed with the respective lens frame.

7. The swimming goggle structure as claimed in claim 5, wherein the connection portion comprises a circumferential slot sized to fit onto a circumferential rib formed on the lens frame.

8. The, swimming goggle structure as claimed in claim 7, wherein the connection portion has an extension formed on the outer side thereof, the extension having a remote end coupled to the head strap.

9. The swimming goggle structure as claimed in claim 6, wherein each of the lens frames comprises an anti-stretching extension integrally with the outer side thereof, the extension having a remote end coupled to the head strap.

10. The swimming goggle structure as claimed in claim 8, wherein the inflating means comprises a gaseous material inlet opening formed on the extension and a passage extending from the opening through the extension to communicate the hollow cushion body.

11. The swimming goggle structure as claimed in claim 9, wherein the inflating means comprises a gaseous material inlet opening formed on the anti-stretch extension and a passage extending from the opening through the extension to communicate the hollow cushion body.

12. A swimming goggle structure comprising:

a pair of lens frames, each having an inner circumferential slot and an antistretching extension formed on an outer side thereof;

a pair of lenses, each being mounted to each of the lens frames by being received within the receiving slot;

an air cushion pad mounted to one side of each of the lens frames adapted to engage a wearer's face, comprising a connection portion attached to the side of the lens frame and a cushion body connected to the connection portion comprising a hollow sealed configuration hat is collapsible with a gaseous material filled therein, the cushion body having a face engaging surface adapted to be in contact engagement with the wearer's face, the connection portion is made of a first rubber material and the cushion body is made of a second rubber material, the first rubber material being comprised entirely of a material that is thicker and more rigid than the second rubber material; and a head strap connected to the anti-stretching extension of the lens frame.

13. The swimming goggle structure as claimed in claim 12, wherein the face engaging surface of the cushion body has an arc shape to comply with contour of the wearer's face.

14. The swimming goggle structure as claimed in claim 13, wherein the cushion body has a uniform thickness between 0.5–2 mm.

15. The swimming goggle structure as claimed in claim 14, wherein the connection portion is made of a first rubber material having a first color and the cushion body is made of a second rubber material having a second color which is different from the first color.

16. The swimming goggle structure as claimed in claim 15, wherein the cushion body further comprises inflating means, the inflating means comprising a gaseous material inlet opening formed on the extension and a passage extending from the opening through the extension to communicate the hollow cushion body.

\* \* \* \* \*